US011877053B2

(12) United States Patent
Hagihara

(10) Patent No.: US 11,877,053 B2
(45) Date of Patent: Jan. 16, 2024

(54) BOOSTER APPARATUS, IMAGING APPARATUS, ENDOSCOPE AND VOLTAGE CONVERSION CONTROL METHOD

(71) Applicant: OLYMPUS CORPORATION, Tokyo (JP)

(72) Inventor: Yoshio Hagihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 521 days.

(21) Appl. No.: 17/154,006

(22) Filed: Jan. 21, 2021

(65) Prior Publication Data

US 2021/0168287 A1 Jun. 3, 2021

Related U.S. Application Data

(63) Continuation of application No. PCT/JP2019/006407, filed on Feb. 20, 2019.

(30) Foreign Application Priority Data

Jul. 23, 2018 (JP) ................... 2018-137870

(51) Int. Cl.
*H04N 5/232* (2006.01)
*H04N 23/65* (2023.01)
(Continued)

(52) U.S. Cl.
CPC ......... *H04N 23/65* (2023.01); *G02B 23/2484* (2013.01); *H02M 3/07* (2013.01); *H04N 23/555* (2023.01)

(58) Field of Classification Search
CPC ....... H02M 3/07; H04N 23/65; H04N 23/555; G02B 23/2484
(Continued)

(56) References Cited

U.S. PATENT DOCUMENTS

2004/0017247 A1  1/2004  Yasui et al.
2005/0047181 A1  3/2005  Yamamoto et al.
2005/0162214 A1*  7/2005  Fukuda ................. H02M 3/073
                                                        327/536

FOREIGN PATENT DOCUMENTS

JP   H09-294367 A   11/1997
JP   2003-348822 A  12/2003
(Continued)

OTHER PUBLICATIONS

International Search Report dated Apr. 2, 2019 issued in PCT/JP2019/006407.

*Primary Examiner* — Lan Dai T Truong
(74) *Attorney, Agent, or Firm* — Scully, Scott, Murphy & Presser, P.C.

(57) ABSTRACT

A booster apparatus includes a voltage conversion control circuit configured to generate second power supply voltage, based on the ground voltage, first power supply voltage, and a driving clock signal. The voltage conversion control circuit includes: a booster circuit configured to generate the second power supply voltage based on an input booster clock signal; a clock buffer configured to generate the booster clock signal and output the generated booster clock signal to the booster circuit; and a voltage comparator that includes: a first voltage generation circuit configured to generate a first signal with a first voltage level; a second voltage generation circuit configured to generate a second signal with a second voltage level; and a comparator configured to compare the first voltage level and the second voltage level and control input of the driving clock signal to be supplied to the clock buffer based on a comparison result.

10 Claims, 11 Drawing Sheets

(51) Int. Cl.
    *G02B 23/24*     (2006.01)
    *H02M 3/07*     (2006.01)
    *H04N 23/50*     (2023.01)

(58) Field of Classification Search
    USPC .......................................................... 348/65
    See application file for complete search history.

(56) References Cited

FOREIGN PATENT DOCUMENTS

| | | |
|---|---|---|
| JP | 2005-080395 A | 3/2005 |
| JP | 2006-129127 A | 5/2006 |

\* cited by examiner

BOOSTER APPARATUS, IMAGING APPARATUS, ENDOSCOPE AND VOLTAGE CONVERSION CONTROL METHOD

CROSS-REFERENCE TO RELATED APPLICATIONS

This application is a continuation of PCT international application No. PCT/JP2019/006407 filed on Feb. 20, 2019, which designates the United States, incorporated herein by reference, and which claims the benefit of priority from Japanese Patent Application No. 2018-137870, filed on Jul. 23, 2018, incorporated herein by reference.

BACKGROUND

1. Technical Field

The present disclosure relates to a booster apparatus, an imaging apparatus, an endoscope, and a voltage conversion control method that generate an image signal by being inserted in a subject.

2. Related Art

In the related art, a charge-pump booster circuit is used for, for example, generating voltage to write data to a flash memory or delete data, or for a high-voltage generation circuit for liquid crystal display of a video camera, a digital camera, or the like. The charge-pump booster circuit includes a plurality of stages of pumping packets, each of which includes a single capacitor, a diode, and the like and which are connected in series, and generates higher voltage than power supply voltage of, for example, a large scale integration (LSI) chip by boosting each of the pumping packets. For example, a voltage supply circuit described in Japanese Laid-open Patent Publication No. 2006-129127 includes a booster circuit that boosts external power supply voltage, a voltage comparator that detects a boosting voltage level that is output from the booster circuit, a clock buffer that maintains voltage at a predetermined level by supplying a driving clock to the booster circuit, and a control circuit that controls clock input of the clock buffer in accordance with a detection result obtained by a voltage detection unit, and reduces power consumption and occurrence of noise (see Japanese Laid-open Patent Publication No. 2006-129127).

SUMMARY

In some embodiments, a booster apparatus includes a voltage conversion control circuit configured to generate second power supply voltage having lower negative voltage than ground voltage, based on the ground voltage, first power supply voltage having higher voltage than the ground voltage, and a driving clock signal supplied from outside. The voltage conversion control circuit includes: a booster circuit configured to generate the second power supply voltage by boosting a predetermined level of voltage that is input from outside, at an absolute value level based on an input booster clock signal; a clock buffer configured to maintain the second power supply voltage at a predetermined level, generate the booster clock signal based on the driving clock signal, and output the generated booster clock signal to the booster circuit; and a voltage comparator that includes: a first voltage generation circuit configured to generate a first signal with a first voltage level based on the first power supply voltage and the second power supply voltage; a second voltage generation circuit configured to generate a second signal with a second voltage level based on the first power supply voltage and the ground voltage; and a comparator configured to compare the first voltage level and the second voltage level and control input of the driving clock signal to be supplied to the clock buffer based on a comparison result.

In some embodiments, an imaging apparatus includes: the booster apparatus; and an imaging element configured to be driven based on a second power supply voltage generated by the booster circuit.

In some embodiments, an endoscope includes: an insertion portion to be inserted into a subject; a booster apparatus that is arranged on a distal end portion of the insertion portion, the booster apparatus being configured to generate an image signal by capturing an image of the subject; and a connector unit that is arranged on a proximal end side of the insertion portion and that is removably connected to a processor configured to supply ground voltage, first power supply voltage having higher voltage than the ground voltage, and a driving clock signal. The booster apparatus includes a voltage conversion control circuit configured to generate second power supply voltage having lower negative voltage than the ground voltage based on the first power supply voltage and the driving clock signal, and the voltage conversion control circuit includes a booster circuit configured to generate the second power supply voltage by boosting a predetermined level of voltage that is input from outside, at an absolute value level based on an input booster clock signal; a clock buffer configured to maintain the second power supply voltage at a predetermined level, generate the booster clock signal based on the driving clock signal, and output the generated booster clock signal to the booster circuit; and a voltage comparator that includes a first voltage generation circuit configured to generate a first signal with a first voltage level based on the first power supply voltage and the second power supply voltage; a second voltage generation circuit configured to generate a second signal with a second voltage level based on the first power supply voltage and the ground voltage; and a comparator configured to compare the first voltage level and the second voltage level and control input of the driving clock signal to be supplied to the clock buffer based on a comparison result.

In some embodiments, a voltage conversion control method includes: generating second power supply voltage having lower negative voltage than ground voltage, based on ground voltage, first power supply voltage having higher voltage than the ground voltage, and a driving clock signal supplied from outside; generating the second power supply voltage by boosting a predetermined level of voltage that is input from outside, at an absolute value level based on an input booster clock signal; maintaining the second power supply voltage at a predetermined level; generating the booster clock signal based on the driving clock signal; generating a first signal with a first voltage level based on the first power supply voltage and the second power supply voltage; generating a second signal with a second voltage level based on the first power supply voltage and the ground voltage; comparing the first voltage level and the second voltage level; and controlling input of the driving clock signal to be supplied to a clock buffer based on a comparison result.

The above and other features, advantages and technical and industrial significance of this disclosure will be better understood by reading the following detailed description of presently preferred embodiments of the disclosure, when considered in connection with the accompanying drawings.

DETAILED DESCRIPTION

As modes (hereinafter, referred to as "embodiments") for carrying out the present disclosure, an endoscope system including an endoscope that includes an imaging apparatus at a distal end portion of an insertion portion that is inserted into a subject will be described below. The present disclosure is not limited by the embodiments below. Further, in description of the drawings, the same components are denoted by the same reference symbols. Furthermore, it is necessary to note that the drawings are schematic, and a relation between a thickness and a width of each of the components, ratios among the components, and the like are different from actual ones. Moreover, the drawings may include a portion that has different dimensions or ratios.

First Embodiment

Configuration of Endoscope System

Figure 1:
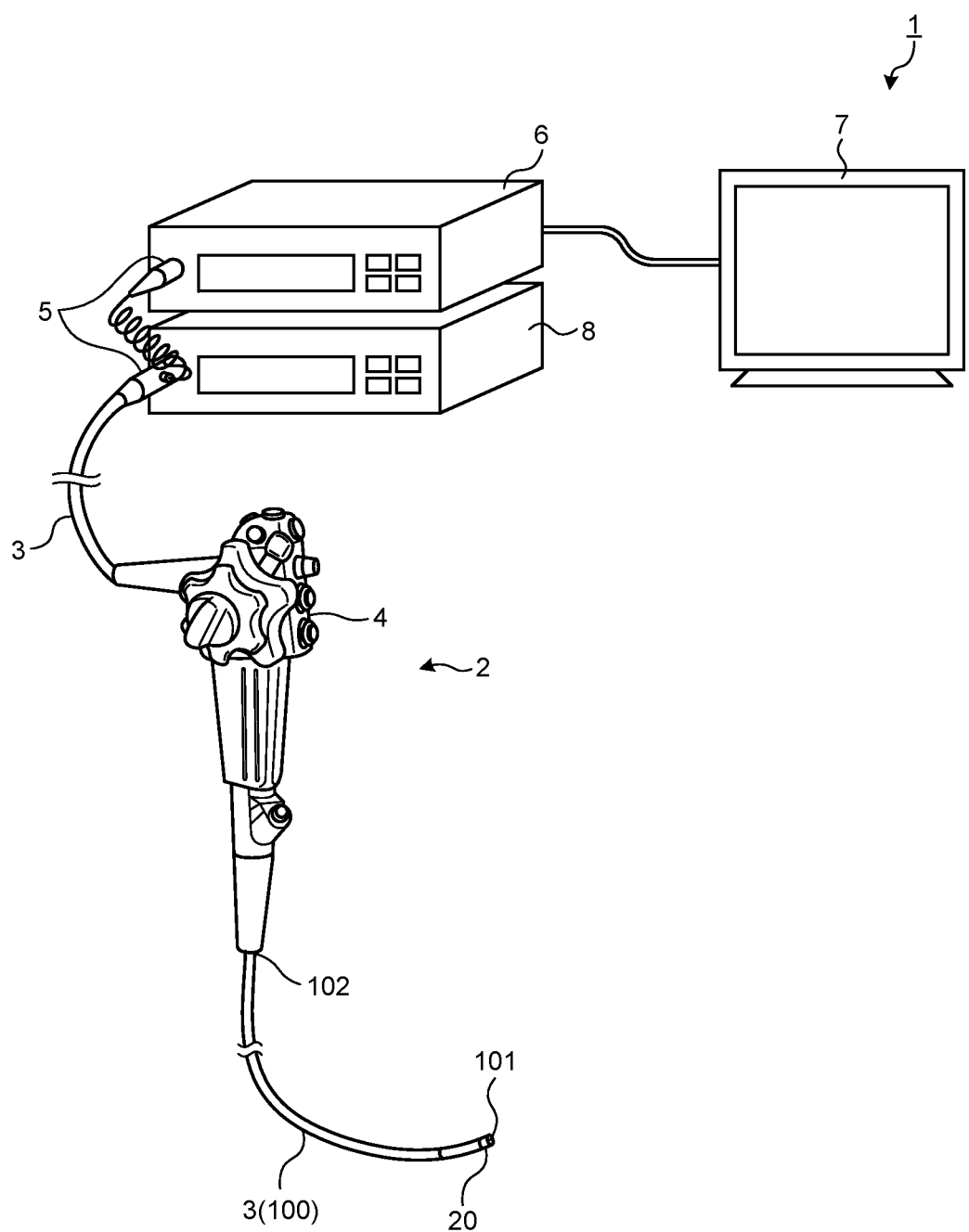
FIG. 1 is an overall diagram schematically illustrating an entire configuration of an endoscope system according to a first embodiment.

FIG. 1 is an overall diagram schematically illustrating an entire configuration of an endoscope system according to a first embodiment. An endoscope system 1 illustrated in FIG. 1 includes an endoscope 2, a transmission cable 3, a connector unit 5, a processor 6, a display device 7, and a light source device 8.

The endoscope 2 captures an image of an inside of a subject by inserting an insertion portion 100 that is a part of the transmission cable 3 into a body cavity of the subject and outputs an imaging signal to the processor 6. Further, the endoscope 2 includes an imaging apparatus 20 that captures an image of the inside of the subject and generates a video signal, on one end side of the transmission cable 3, i.e., at a side of a distal end portion 101 of the insertion portion 100 that is inserted into the body cavity of the subject. Furthermore, the endoscope 2 includes an operating unit 4 that receives various kinds of operation on the endoscope 2, at a side of a proximal end portion 102 of the insertion portion 100. The video signal of an in-vivo image captured by the imaging apparatus 20 is output to the connector unit 5 via the transmission cable 3 with a length of a few meters (m), for example.

The transmission cable 3 connects the endoscope 2 to the connector unit 5 and connects the endoscope 2 to the processor 6 and the light source device 8. Further, the transmission cable 3 transmits the imaging signal generated by the imaging apparatus 20 to the connector unit 5. The transmission cable 3 is configured with a cable, an optical fiber, or the like.

The connector unit 5 is connected to the endoscope 2, the processor 6, and the light source device 8, performs predetermined signal processing on the video signal output by the connected endoscope 2, and outputs the video signal to the processor 6.

The processor 6 performs predetermined image processing on the video signal input from the connector unit 5, and outputs the video signal to the display device 7. Further, the processor 6 comprehensively controls the entire endoscope system 1. For example, the processor 6 changes illumination light that is emitted by the light source device 8, or changes an imaging mode of the endoscope 2.

The display device 7 displays an image corresponding to the video signal that is subjected to the image processing by the processor 6. Further, the display device 7 displays various kinds of information on the endoscope system 1. The display device 7 is configured with a display panel made of liquid crystal, organic electro luminescence (EL), or the like.

The light source device 8 emits illumination light toward a subject (imaging object) from the distal end portion 101 side of the insertion portion 100 of the endoscope 2 via the connector unit 5 and the transmission cable 3. The light source device 8 is configured with a white light emitting diode (LED) that emits white light. Meanwhile, in the present embodiment, a simultaneous illumination method is adopted to the light source device 8, but it may be possible to adopt a frame sequential illumination method.

Main Part of Endoscope System

Figure 2:
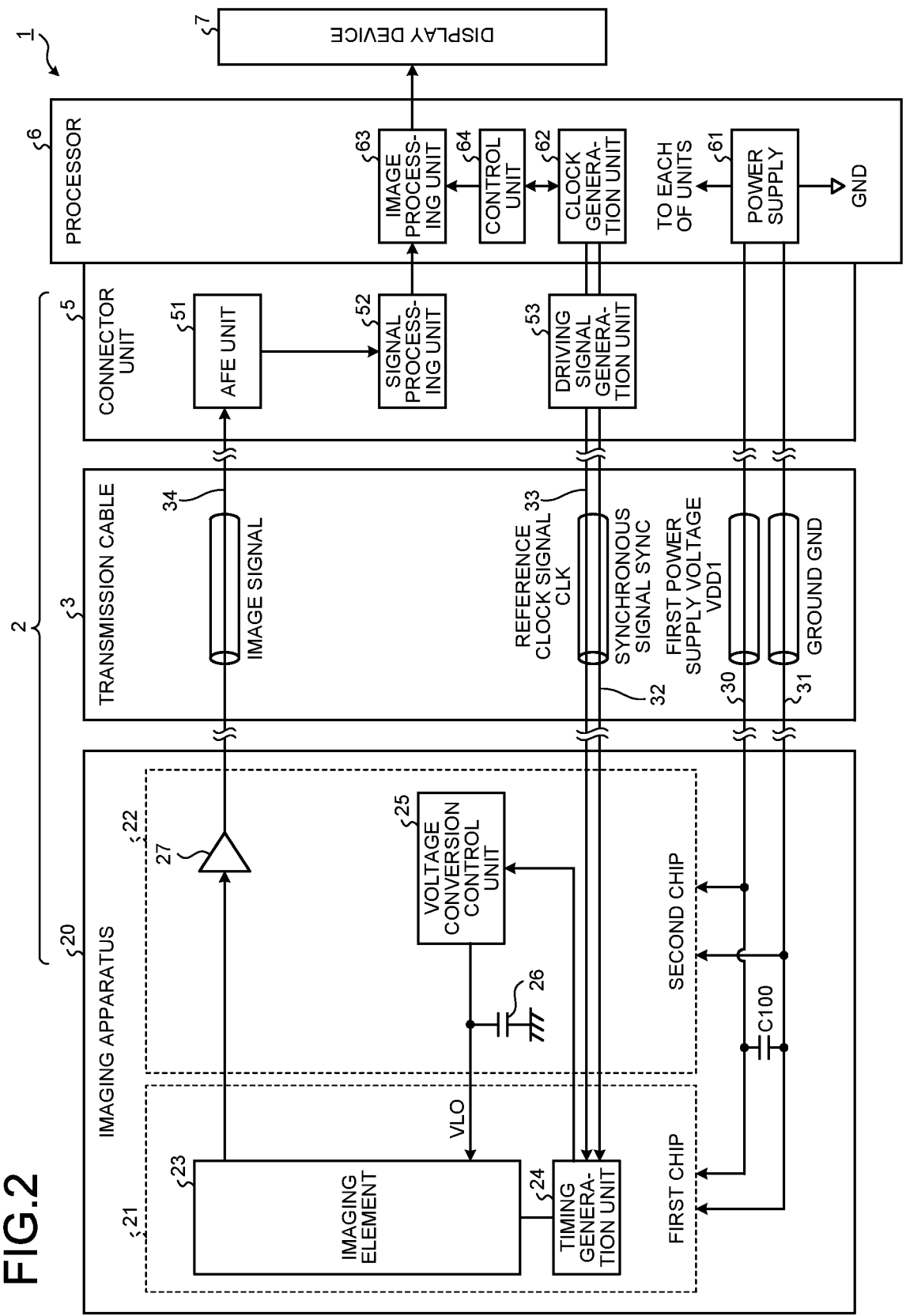
FIG. 2 is a block diagram illustrating a functional configuration of a main part of the endoscope system according to the first embodiment.

Functions of a main part of the endoscope system 1 will be described below. FIG. 2 is a block diagram illustrating a functional configuration of the main part of the endoscope system 1.

Configuration of Endoscope

A configuration of the endoscope 2 will be described below.

The endoscope 2 illustrated in FIG. 2 includes the imaging apparatus 20, the transmission cable 3, and the connector unit 5.

Figure 3:
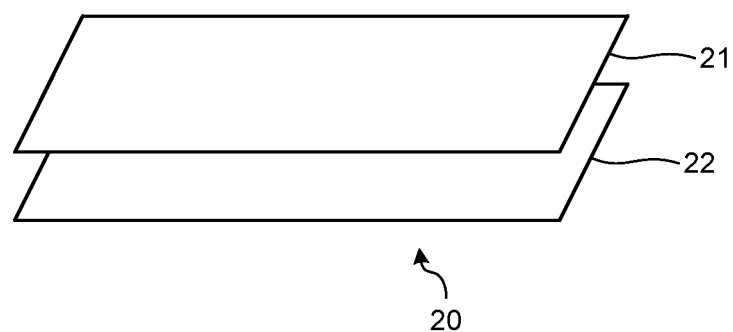
FIG. 3 is a diagram schematically illustrating arrangement of a first chip and a second chip according to the first embodiment.

The imaging apparatus 20 includes a first chip 21 and a second chip 22. As illustrated in FIG. 3, the imaging apparatus 20 is formed such that the first chip 21 is stacked on the second chip 22 and attached in an opposing manner by Cu—Cu bonding or the like. Further, the chips are connected to each other by a pad that is arranged on an edge portion of each of the chip, a via that penetrates through the chips, or the like. Meanwhile, the first chip 21 and the second chip 22 need not always be arranged such that principal surfaces of the chips are parallel to each other, but may be arranged side by side or may be arranged such that one of the principal surfaces is perpendicular to the other one of the principal surfaces, depending on a peripheral configuration.

First, the first chip 21 will be described.

The first chip 21 includes an imaging element 23 and a timing generation unit 24.

The imaging element 23 receives light of an object image collected by an optical system (not illustrated), performs photoelectric conversion, and generates an image signal through the photoelectric conversion. The imaging element 23 includes a plurality of pixels that generate image signals depending on received light intensity and that are arranged in a two-dimensional matrix manner in matrix directions. The imaging element 23 is configured with an image sensor, such as a charge coupled device (CCD) or a complementary metal oxide semiconductor (CMOS). Further, the imaging element 23 is driven by power supply voltage VDD that is input from the processor 6 via the transmission cable 3 and by second power supply voltage VLO that is input from the second chip 22 (to be described later). In the first embodiment, the power supply voltage VDD and first power supply voltage VDD1 are the same. Meanwhile, a detailed configuration of the imaging element 23 will be described later.

The timing generation unit 24 generates a driving signal for driving the imaging element 23, a voltage conversion control circuit 25 of the second chip 22 (to be described later), or the like on the basis of a reference clock signal CLK and a synchronous signal SYNC that are input through the transmission cable 3. The timing generation unit 24 outputs the driving signal to the imaging element 23 and the voltage conversion control circuit 25. The timing generation unit 24 is configured with a timing generator or the like.

Next, the second chip 22 will be described.

The second chip 22 includes the voltage conversion control circuit 25, a capacitor 26, and a buffer unit 27.

The voltage conversion control circuit 25 converts voltage of the first power supply voltage VDD1 that is input from the processor 6 via the transmission cable 3 and generates the second power supply voltage VLO (negative voltage) under the control of the timing generation unit 24. The voltage conversion control circuit 25 outputs the second power supply voltage VLO to the imaging element 23 of the first chip 21. Meanwhile, a detailed configuration of the voltage conversion control circuit 25 will be described later.

One end of the capacitor 26 is connected to ground voltage GND, and the other end is connected to a signal line that connects the voltage conversion control circuit 25 and the first chip 21. The capacitor 26 functions as an external capacitance for stabilizing the second power supply voltage VLO that is supplied by the voltage conversion control circuit 25.

The buffer unit 27 amplifies the image signal input from the imaging element 23 and outputs the image signal to the transmission cable 3. The buffer unit 27 is configured with an output amplifier or the like.

Configuration of Transmission Cable

The transmission cable 3 will be described below.

The transmission cable 3 is configured with a plurality of signal lines and a light guide (not illustrated). Specifically, the transmission cable 3 includes a ground line 30 for transmitting the ground voltage GND, a signal line 31 for transmitting the power supply voltage VDD (the first power supply voltage VDD1), a signal line 32 for transmitting the synchronous signal SYNC, a signal line 33 for transmitting the reference clock signal CLK, and a signal line 34 for transmitting the image signal.

Configuration of Connector

A configuration of the connector unit 5 will be described below.

The connector unit 5 includes an analog front end unit 51 (hereinafter, referred to as the "AFE unit 51"), a signal processing unit 52, and a driving signal generation unit 53. Meanwhile, the AFE unit 51, the signal processing unit 52, and the driving signal generation unit 53 are implemented by using a field programmable gate array (FPGA), for example.

The AFE unit 51 performs a process, such as noise reduction and A/D conversion, on the image signal transmitted through the transmission cable 3, and outputs a digital image signal to the signal processing unit 52.

The signal processing unit 52 performs predetermined signal processing, such as a format conversion process or a gain-up process, on the digital image signal input from the AFE unit 51, and outputs the digital image signal to the processor 6.

The driving signal generation unit 53 generates the reference clock signal CLK and the synchronous signal SYNC for driving the imaging apparatus 20, on the basis of a clock signal input from the processor 6. The driving signal generation unit 53 outputs the reference clock signal CLK and the synchronous signal SYNC to the transmission cable 3.

Configuration of Processor

A configuration of the processor 6 will be described below.

The processor 6 includes a power supply 61, a clock generation unit 62, an image processing unit 63, and a control unit 64.

The power supply 61 generates the first power supply voltage VDD1 that is based on the ground voltage GND, on the basis of electric power input from outside. The power supply 61 outputs the first power supply voltage VDD1 and the ground voltage GND to the transmission cable 3 and each of the units included in the processor 6.

The clock generation unit 62 generates a clock signal that is used as a reference for operation of each of the units of the endoscope system 1, and outputs the clock signal to the driving signal generation unit 53 of the connector unit 5 and the control unit 64. The clock generation unit 62 is configured with a clock module or the like.

The image processing unit 63 performs predetermined image processing on the image signal input from the signal processing unit 52 of the connector unit 5 and outputs the image signal to the display device 7, under the control of the control unit 64. Here, examples of the predetermined image processing include a white balance adjustment process and a demosaicing process. The image processing unit 63 is configured with a graphics processing unit (GPU), an FPGA, or the like.

The control unit 64 controls each of the units of the endoscope system 1. The control unit 64 is configured with a central processing unit (CPU), a memory, and the like.

Configuration of Imaging Element and Voltage Conversion Control Circuit

Figure 4:
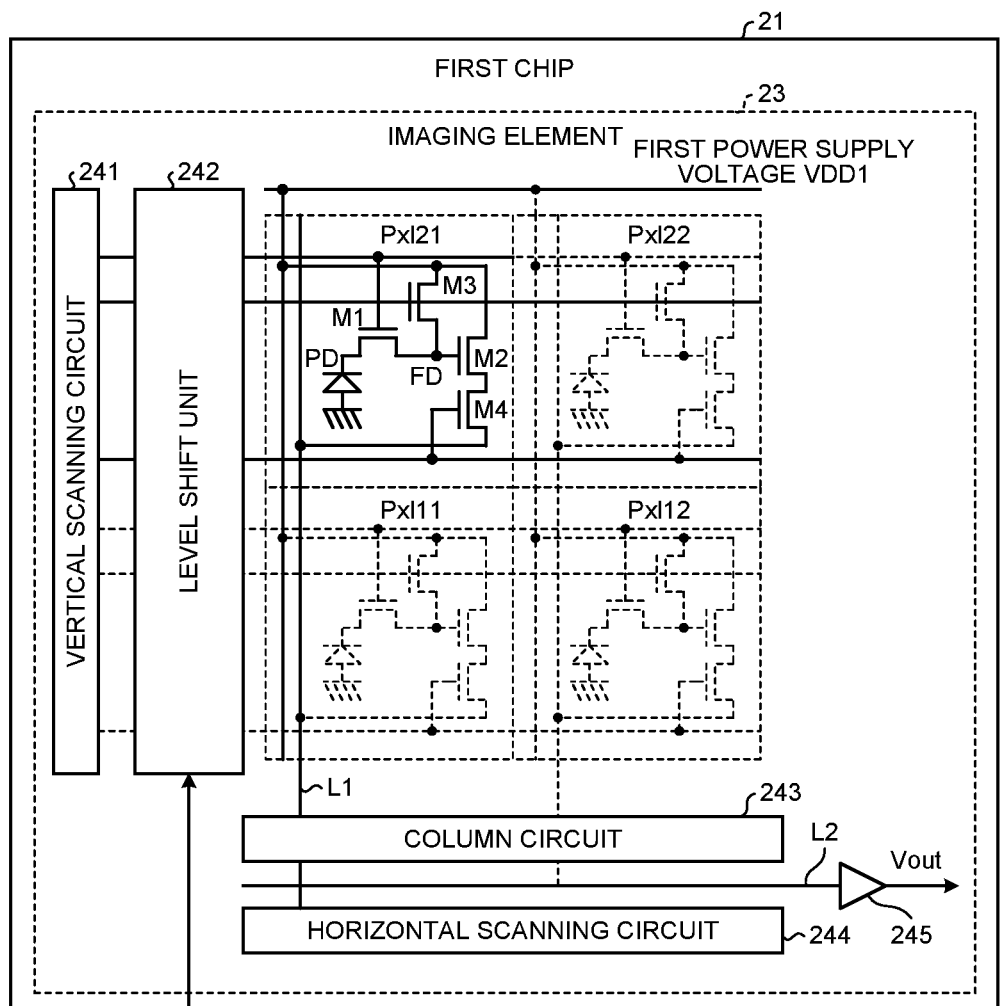
FIG. 4 is a schematic diagram illustrating a configuration of a main part of an imaging element and a voltage conversion control circuit according to the first embodiment.
Figure 4:
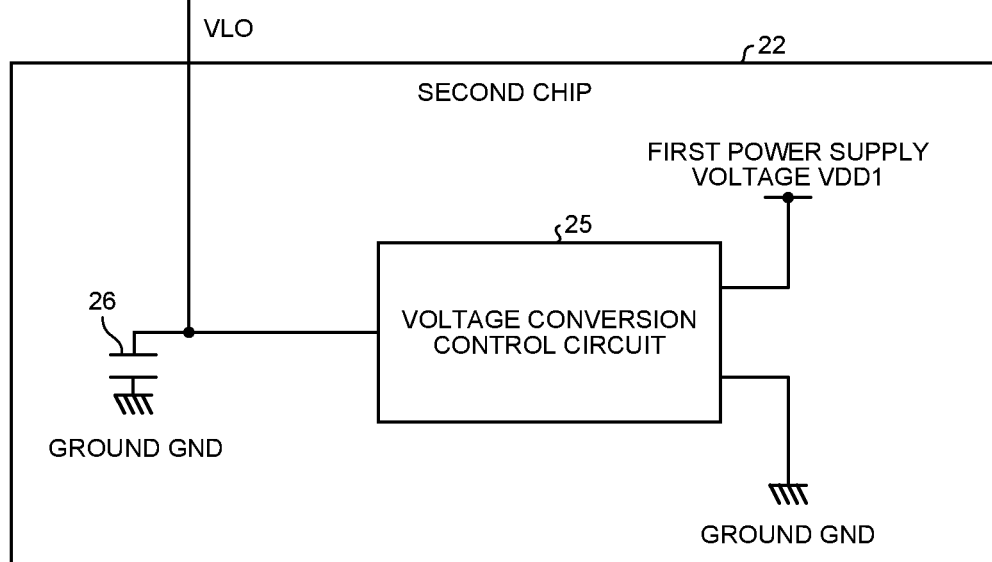

A configuration of a main part of the imaging element 23 and the voltage conversion control circuit 25 as described above will be described below. FIG. 4 is a schematic diagram illustrating the configuration of the main part of the imaging element 23 and the voltage conversion control circuit 25.

Imaging Element

A configuration of the imaging element 23 will be described below. As illustrated in FIG. 4, the imaging element 23 includes a plurality of pixels Px111, Px112, Px121, and Px122, a vertical scanning circuit 241, a level shift unit 242, a column circuit 243, a horizontal scanning circuit 244, and an output amplifier 245. The four pixels Px111, Px112, Px121, and Px122 that are arranged in 2×2 are illustrated in FIG. 4 for simplicity of explanation, but a plurality of the above-described pixels are arranged in a two-dimensional matrix manner. Meanwhile, all of the four pixels Px111, Px112, Px121, and Px122 have the same configuration, and therefore, the pixel Px121 will be described below. Further, if any one of the four pixels Px111, Px112, Px121, and Px122 is described, the pixel is simply referred to as the pixel Px1.

The pixel Px121 includes a photodiode PD, a transfer transistor M1, a floating diffusion FD, an amplification transistor M2, a reset transistor M3, and a row selection transistor M4.

The photodiode PD receives input light, performs photoelectric conversion to a signal charge amount in accordance with the amount of incident light, and accumulates charges. A cathode side of the photodiode PD is connected to the transfer transistor M1, and an anode side is connected to the ground voltage GND.

The transfer transistor M1 transfers a signal charge from the photodiode PD to the floating diffusion FD. A gate of the transfer transistor M1 is connected to a signal line for supplying a transfer signal, one end side is connected to the photodiode PD, and the other end side is connected to the floating diffusion FD. The transfer transistor M1 enters an ON state if a voltage level of the transfer signal that is input from the vertical scanning circuit 241 and the level shift unit 242 (to be described later) reaches a High state, and transfers a signal charge from the photodiode PD to the floating diffusion FD. Further, the transfer transistor M1 enters an OFF state if the voltage level of the transfer signal that is input from the vertical scanning circuit 241 and the level shift unit 242 (to be described later) reaches a Low state, and the photodiode PD accumulates charges. Meanwhile, the voltage level of the transfer signal in the High state is the first power supply voltage VDD1, and the voltage level in the Low state is the second power supply voltage VLO.

The floating diffusion FD converts the signal charge accumulated in the photodiode PD to voltage. The floating diffusion FD is formed of a floating diffusion capacitance.

The amplification transistor M2 amplifies the signal converted by the floating diffusion FD, and outputs the amplified signal to the row selection transistor M4. A gate of the amplification transistor M2 is connected to the floating diffusion FD, one end side is connected to the first power supply voltage VDD1, and the other end side is connected to the row selection transistor M4.

The reset transistor M3 resets the floating diffusion FD to a predetermined potential. A gate of the reset transistor M3 is connected to the signal line for supplying a reset signal, one end side is connected to the first power supply voltage VDD1, and the other end side is connected to the gate of the amplification transistor M2. The reset transistor M3 enters an ON state if the voltage level of the reset signal that is input from the vertical scanning circuit 241 and the level shift unit 242 (to be described later) reaches the High state, and discharges the signal charge accumulated in the floating diffusion FD to the first power supply voltage VDD1, to thereby reset the floating diffusion FD to the predetermined potential. The reset transistor M3 enters an OFF state if the voltage level of the reset signal reaches the Low state, and the floating diffusion FD is enabled to accumulate a signal charge.

The row selection transistor M4 transfers a signal input from the amplification transistor M2 to a vertical signal line L1. A gate of the row selection transistor M4 is connected to a signal line for supplying a row selection signal, one end side is connected to the amplification transistor M2, and the other end side is connected to the vertical signal line L1. The row selection transistor M4 enters an ON state if the voltage level of the row selection signal input from the vertical scanning circuit 241 and the level shift unit 242 (to be described later) reaches the High state, and transfers the signal input from the amplification transistor M2 to the vertical signal line L1.

The vertical scanning circuit 241 supplies various signals including the transfer signal or the selection signal to the signal line of a selected pixel row of the pixel Px1 and outputs the image signal or the like to the vertical signal line L1 under the control of the timing generation unit 24. The vertical scanning circuit 241 is configured with an address decoder or the like, for example.

The level shift unit 242 shifts voltage levels of various signals input from the vertical scanning circuit 241 to certain voltage levels that are needed to drive each of the transistors included in each of the pixels Px1, and outputs the various signals. The level shift unit 242 is configured with a level shift circuit.

The column circuit 243 performs, on the basis of the signal input from the horizontal scanning circuit 244, a process for cancelling out characteristics variation among the pixels Px1 or a noise removal process with respect to the image signal that is transferred through the vertical signal line L1, and outputs the image signal to the horizontal signal line L2. The column circuit 243 is configured with a plurality of transistors, for example.

The horizontal scanning circuit 244 performs selection operation of selecting the column circuit 243 in predetermined order and sequentially outputs image signals from each of the pixel rows to the output amplifier 245 under the control of the timing generation unit 24. The horizontal scanning circuit 244 is configured with a shift register, an address decoder, or the like, for example.

The output amplifier 245 amplifies the image signal input through the horizontal signal line L2, and outputs the amplified image signal to the second chip 22. The output amplifier 245 is configured with an amplification amplifier, such as an operational amplifier.

Voltage Conversion Control Circuit

A configuration of the voltage conversion control circuit 25 will be described below.

The voltage conversion control circuit 25 generates the second power supply voltage VLO by converting voltage of the first power supply voltage VDD1, which is input from the processor 6 through the transmission cable 3, under the control of the timing generation unit 24. The voltage conversion control circuit 25 outputs the second power supply voltage VLO to the level shift unit 242.

Figure 5:
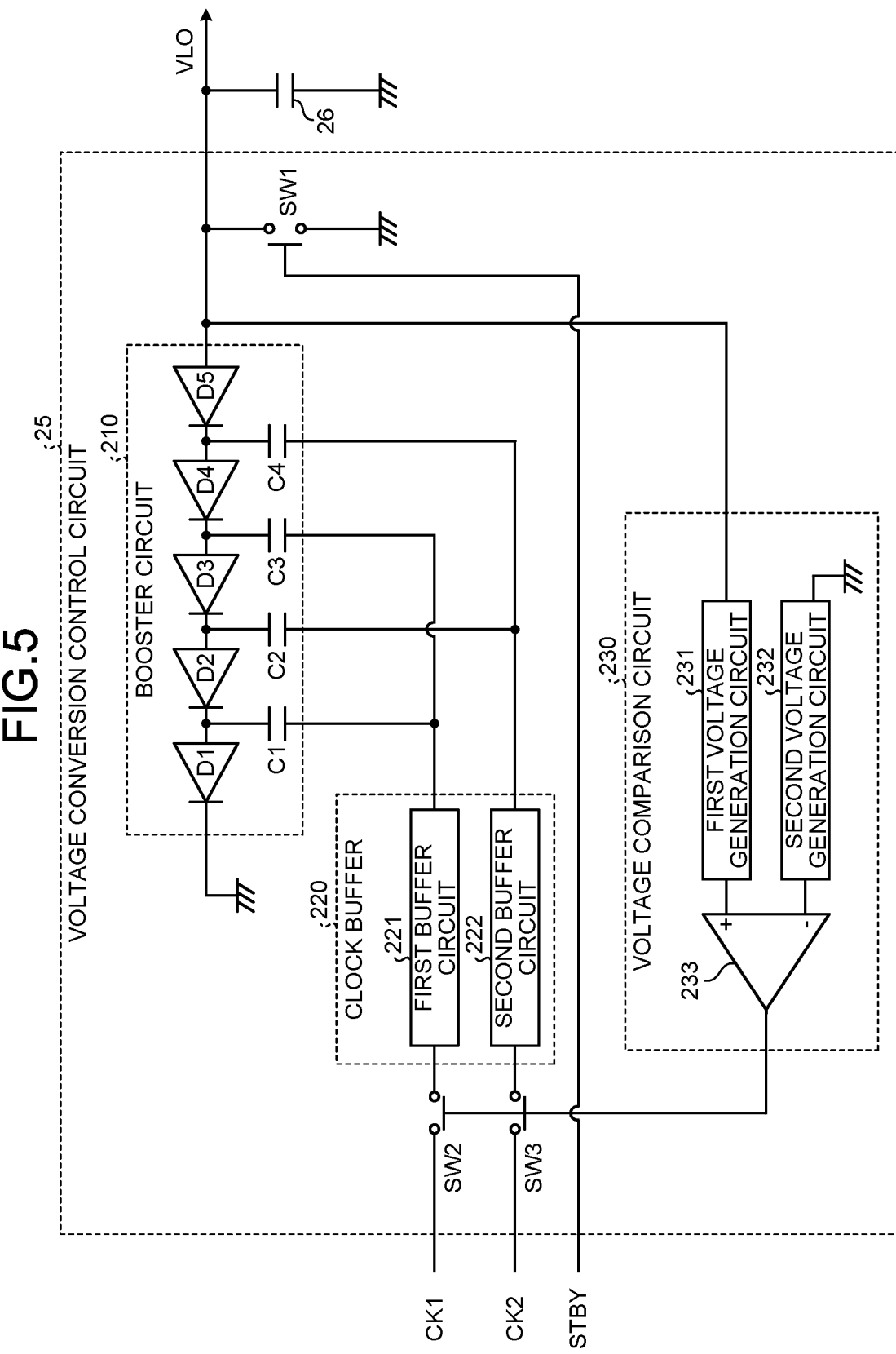
FIG. 5 is a diagram illustrating a detailed configuration of the voltage conversion control circuit according to the first embodiment.

FIG. 5 is a diagram illustrating a detailed configuration of the voltage conversion control circuit 25. The voltage conversion control circuit 25 illustrated in FIG. 5 includes a booster circuit 210, a clock buffer 220, a voltage comparison unit 230, a switch SW1, a switch SW2, and a switch SW3. Meanwhile, the switches SW1 to SW3 are configured with transistors, for example.

The booster circuit 210 receives input of a booster clock and a predetermined level of voltage, increases (boosts) an absolute value of the predetermined level of voltage, and generates the second power supply voltage VLO having lower negative voltage than the ground voltage GND. The booster circuit 210 is a charge pump booster circuit configured with a capacitor C1 to a capacitor C4 and a diode D1 to a diode D5.

The clock buffer 220 drives a pumping capacitor of the booster circuit 210. Specifically, the clock buffer 220 generates the booster clock based on a driving clock signal CK1 and a driving clock signal CK2 that are input from the timing generation unit 24, outputs the booster clock to the booster circuit 210, and holds the second power supply voltage VLO. Further, the clock buffer 220 includes a first buffer circuit 221 to which the driving clock signal CK1 is input and a second buffer circuit 222 to which the driving clock signal CK2 is input.

One end side of the first buffer circuit 221 is connected to the switch SW2, and the other end side is connected to the capacitor C1 and the capacitor C3.

One end side of the second buffer circuit 222 is connected to the switch SW3, and the other end side is connected to the capacitor C2 and the capacitor C4.

The voltage comparison unit 230 detects an output voltage level of the booster circuit 210, controls ON and OFF of the switch SW2 and the switch SW3 on the basis of a detection result, and controls the driving clock signal CK1 and the driving clock signal CK2 that are supplied to the clock buffer 220. The voltage comparison unit 230 includes a first voltage generation circuit 231, a second voltage generation circuit 232, and a comparator 233.

Figure 6:
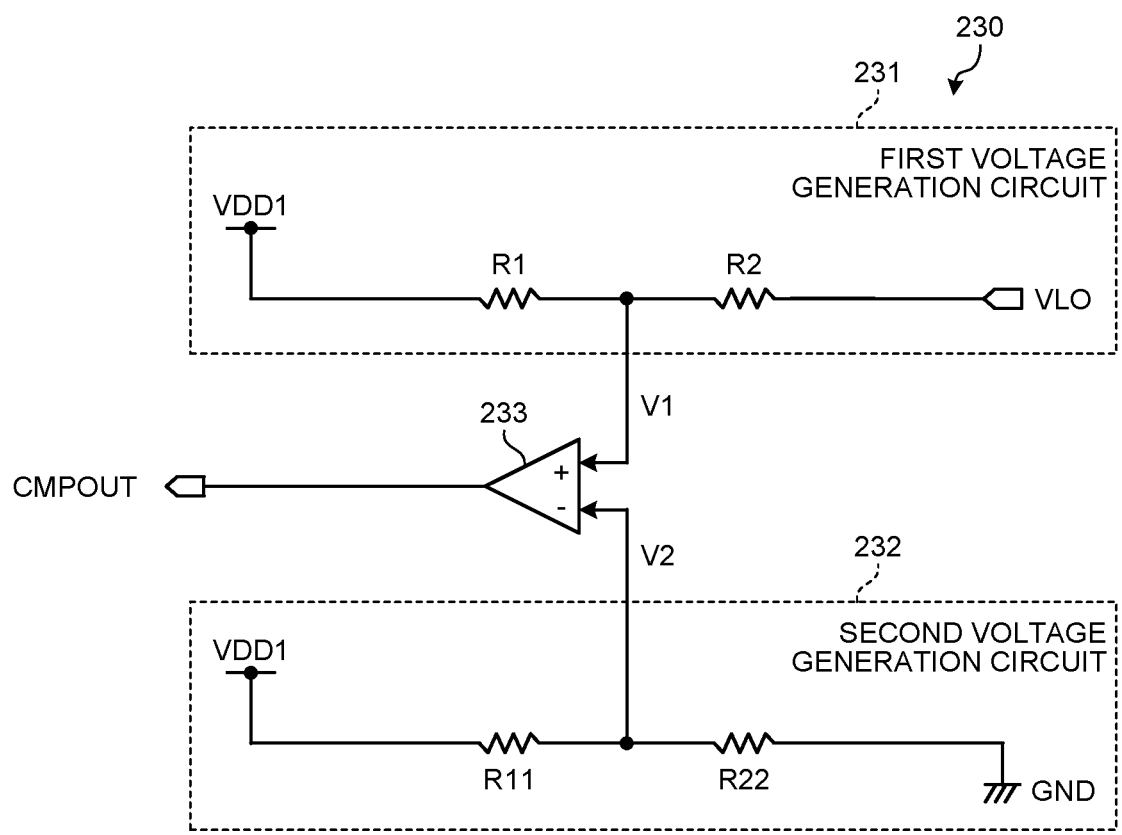
FIG. 6 is a diagram illustrating a circuit configuration of a voltage comparison unit according to the first embodiment.

FIG. 6 is a diagram illustrating a circuit configuration of the voltage comparison unit 230. As illustrated in FIG. 6, the first voltage generation circuit 231 includes at least a single resistance between the first power supply voltage VDD1 and the second power supply voltage VLO that is booster voltage. Specifically, the first voltage generation circuit 231 includes a resistance R1 and a resistance R2. The resistance R1 and the resistance R2 are arranged between a first terminal of the first power supply voltage VDD1 and a second terminal of the second power supply voltage VLO. The resistance R1 and the resistance R2 electrically connect the first terminal and the second terminal, and perform resistance voltage dividing on a voltage difference between the first power supply voltage VDD1 and the second power supply voltage VLO, to thereby generate a first signal for which level shift to a first voltage level V1 that is a preferable voltage level is performed. Specifically, the first voltage level V1 is represented by Expression (1) below.

$$V1=(R2/(R1+R2))\times(VDD1-VLO)+VLO \quad (1)$$

The second voltage generation circuit 232 includes at least a single resistance between the first power supply voltage VDD1 and the ground voltage GND (ground voltage VSS). Specifically, the second voltage generation circuit 232 includes a resistance R11 and a resistance R22. The resistance R11 and the resistance R22 are arranged between the first terminal of the first power supply voltage VDD1 and a ground terminal of the ground voltage GND. Further, a combined resistance value of the resistance R11 and the resistance R22 is equal to or larger than a predetermined multiple of a combined resistance value of the resistance R1 and the resistance R2. Specifically, the combined resistance value of the resistance R11 and the resistance R22 is equal to or larger than one-tenth of the combined resistance value of the resistance R1 and the resistance R2. Furthermore, the resistance R1, the resistance R2, the resistance R11, and the resistance R22 are configured with the same kind of resistance element. Moreover, the resistance R11 and the resistance R22 electrically connect the first terminal and the ground terminal, and perform resistance voltage dividing on a voltage difference between the first power supply voltage VDD1 and the ground voltage GND, to thereby generate a second signal for which level shift to a second voltage level V2 that is a preferable voltage level is performed. Specifically, the second voltage level V2 is represented by Expression (2) below.

$$V2=(R12/(R11+R12))\times(VDD1-VSS)+VSS \quad (2)$$

The comparator 233 compares the first voltage level V1 of the first signal input from the first voltage generation circuit 231 and the second voltage level V2 of the second signal input from the second voltage generation circuit 232, and outputs a comparison result to the switch SW1 and the switch SW2. Specifically, the comparator 233 outputs a signal in the High state if the first voltage level V1 of the first signal is higher than the second voltage level V2 of the second signal, and outputs a signal in the Low state if the first voltage level V1 of the first signal is equal to or lower than the second voltage level V2 of the second signal. Accordingly, each of the first voltage V1 and the second voltage V2 has a fluctuation component in phase with a fluctuation component ($\Delta$VDD1) of the first power supply voltage VDD1. As a result, it is possible to improve PSRR with respect to the first power supply voltage VDD1.

Referring back to FIG. 5, the configuration of the voltage conversion control circuit 25 will be described.

If a standby signal STBY for setting a standby mode is input from the timing generation unit 24, the switch SW1 fixes the second power supply voltage VLO that is output from the booster circuit 210, to thereby stabilize the second power supply voltage VLO that is output from the booster circuit 210. Here, the standby mode indicates a state in which the first power supply voltage VDD1 itself is supplied to a subsequent circuit, such as the first chip 21, due to suspension of operation of the voltage conversion control circuit 25, but power supply to the subsequent circuit is blocked due to suspension of the operation of the voltage conversion control circuit 25.

According to the first embodiment as described above, it is possible to generate the negative voltage VLO with high PSRR by a simple configuration, by generating the second voltage V2 on the basis of the ground voltage GND and the first power supply voltage VDD1 that are supplied from the processor 6 via the transmission cable 3, so that it is possible to reduce a size of the imaging apparatus 20.

Further, according to the first embodiment, it is possible to substantially equalize a fluctuation in the first voltage level V1 and a fluctuation in the second voltage level V2 in accordance with a fluctuation in the first power supply voltage VDD1, so that it is possible to easily maintain the booster voltage at a predetermined voltage level. In contrast, in a case in which the second voltage level V2, which is configured using output voltage from a bandgap reference circuit for example, with the first voltage level V1, which is changed in accordance with the first power supply voltage VDD1 and the booster voltage, a fluctuation of the first voltage level V1 that depends on a fluctuation of the first power supply voltage VDD1 extremely increases as compared to a fluctuation of the second voltage level V2, so that PSRR is largely reduced.

Second Embodiment

A second embodiment will be described below. The second embodiment is different in terms of the configuration of the voltage comparison unit 230 according to the first embodiment. In the following, a voltage comparison unit according to the second embodiment will be described. Meanwhile, the same components as those of the endoscope system 1 according to the first embodiment as described above are denoted by the same reference symbols, and detailed explanation thereof will be omitted.

Configuration of Voltage Comparison Unit

Figure 7:
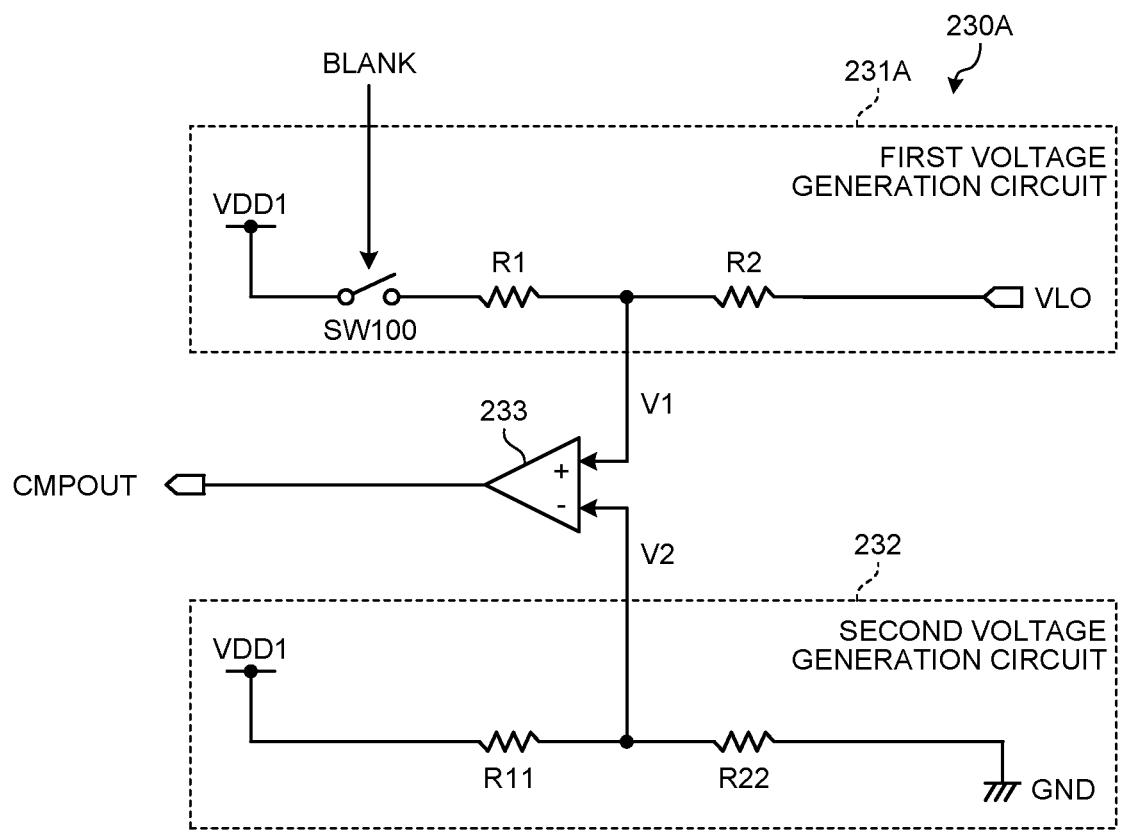
FIG. 7 is a diagram illustrating a circuit configuration of a voltage comparison unit according to a second embodiment.

FIG. 7 is a diagram illustrating a circuit configuration of the voltage comparison unit according to the second embodiment. A voltage comparison unit 230A illustrated in FIG. 7 includes a first voltage generation circuit 231A, instead of the first voltage generation circuit 231 of the voltage comparison unit 230 according to the first embodiment as described above.

The first voltage generation circuit 231A includes a switch SW100 between the first terminal of the first power supply voltage VDD1 and the resistance R1, in addition to the components of the first voltage generation circuit 231 according to the first embodiment as described above.

The switch SW100 is configured with a PMOS transistor, for example. The switch SW100 enters an ON state during a boosting period of the booster circuit 210 and enters an OFF state during other periods, on the basis of a signal that is input from the timing generation unit 24. Accordingly, it is possible to prevent an unnecessary fluctuation of the first voltage level (V1) due to a leak current during a period other than the boosting period of the booster circuit 210. Here, the boosting period is a blanking period of the imaging element 23, and other periods are periods during which the imaging element 23 outputs the image signal.

According to the second embodiment as described above, the switch SW100 enters the ON state during the boosting period of the booster circuit 210 (blanking period) on the basis of the signal that is input from the timing generation unit 24, and enters an OFF state during other periods, so that it is possible to prevent an unnecessary fluctuation of the first voltage level (V1) due to a leak current during a period other than the boosting period of the booster circuit 210.

Meanwhile, in the second embodiment, the switch SW100 is arranged between the first terminal of the first power supply voltage VDD1 and the resistance R1, but may be arranged between the second terminal of the second power supply voltage VLO and the resistance R2, for example.

Third Embodiment

A third embodiment will be described below. A third embodiment is different in terms of the configuration of the endoscope system 1 according to the first embodiment as described above. In the following, a configuration of an endoscope system according to the third embodiment will be described. Meanwhile, the same components as those of the endoscope system 1 according to the first embodiment as described above are denoted by the same reference symbols, and detailed explanation thereof will be omitted.

Configuration of Endoscope System

Figure 8:
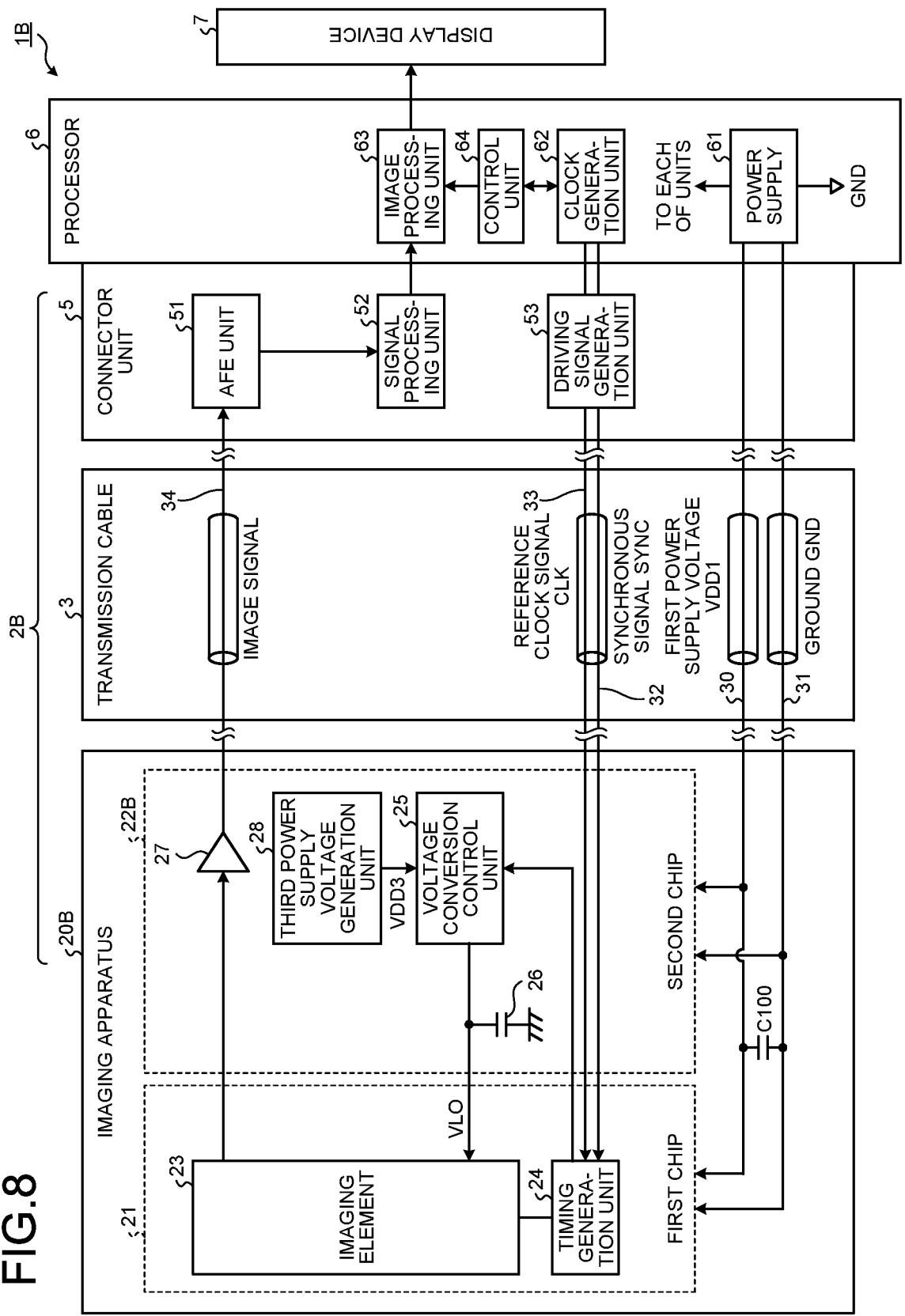
FIG. 8 is a block diagram illustrating a functional configuration of an endoscope system according to a third embodiment.

FIG. 8 is a block diagram illustrating a functional configuration of the endoscope system according to the third embodiment. An endoscope system 1B illustrated in FIG. 8 includes an endoscope 2B instead of the endoscope 2 according to the first embodiment. Further, the endoscope 2B includes an imaging apparatus 20B instead of the imaging apparatus 20 according to the first embodiment as described above. Furthermore, the imaging apparatus 20B includes a second chip 22B instead of the second chip 22 according to the first embodiment as described above.

The second chip 22B further includes a third power supply voltage generation unit 28 in addition to the components of the second chip 22 according to the first embodiment as described above.

The third power supply voltage generation unit 28 generates third power supply voltage VDD3 (VDD1>VDD3) that is lower by predetermined voltage than the power supply voltage VDD (the same as the first power supply voltage VDD1 in the third embodiment) that is input from the processor 6 via the transmission cable 3, and the third power supply voltage VDD3 is output to a part of circuits included in the voltage conversion control circuit 25.

Figure 9:
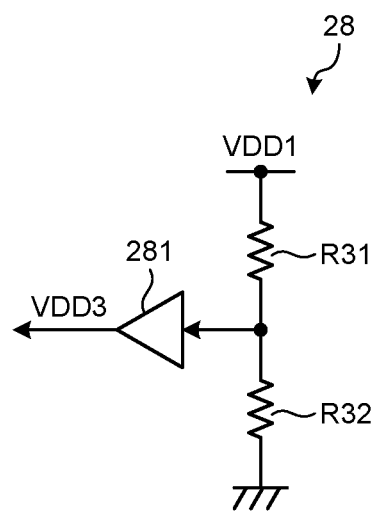
FIG. 9 is a diagram illustrating a circuit configuration of a third power supply voltage generation unit according to the third embodiment.

FIG. 9 is a diagram illustrating a circuit configuration of the third power supply voltage generation unit 28. As illustrated in FIG. 9, the third power supply voltage generation unit 28 includes a resistance R31 and a resistance R32 between the first terminal of the first power supply voltage VDD1 and the ground terminal of the ground voltage GND. Further, the third power supply voltage generation unit 28 includes a buffer 281. The third power supply voltage generation unit 28 performs resistance voltage dividing on a voltage difference between the first power supply voltage VDD1 and the ground voltage GND by using the resistance R31 and the resistance R32, and amplifies the voltage subjected to the resistance voltage dividing by using the buffer 281, to thereby generate the third power supply voltage VDD3. The generated third power supply VDD3 is used as a power supply of the comparator 233, for example.

According to the third embodiment as described above, in a case in which the first chip 21 is manufactured by using a relatively high withstand voltage semiconductor process for arranging a transistor capable of operating at any of a voltage difference among the first power supply voltage VDD1, the ground voltage GND, and the second power supply voltage VLO, even if only a transistor with withstand voltage equal to about a voltage difference between the first power supply voltage VDD1 and the ground voltage GND can be arranged through the semiconductor process used to manufacture the second chip 22B, because the third power supply voltage generation unit 28 generates the third power supply voltage VDD3 that is lower by the predetermined voltage than the first power supply voltage VDD1, it is possible to arrange the voltage conversion control circuit 25 on the second chip 22B without using the high withstand voltage semiconductor process.

Fourth Embodiment

A fourth embodiment will be described below. The fourth embodiment is different in terms of the configuration of the endoscope system 1B according to the third embodiment. In the following, a configuration of an endoscope system according to the fourth embodiment will be described. Meanwhile, the same components as those of the endoscope system 1B according to the third embodiment as described above are denoted by the same reference symbols, and detailed explanation thereof will be omitted.

Figure 10:
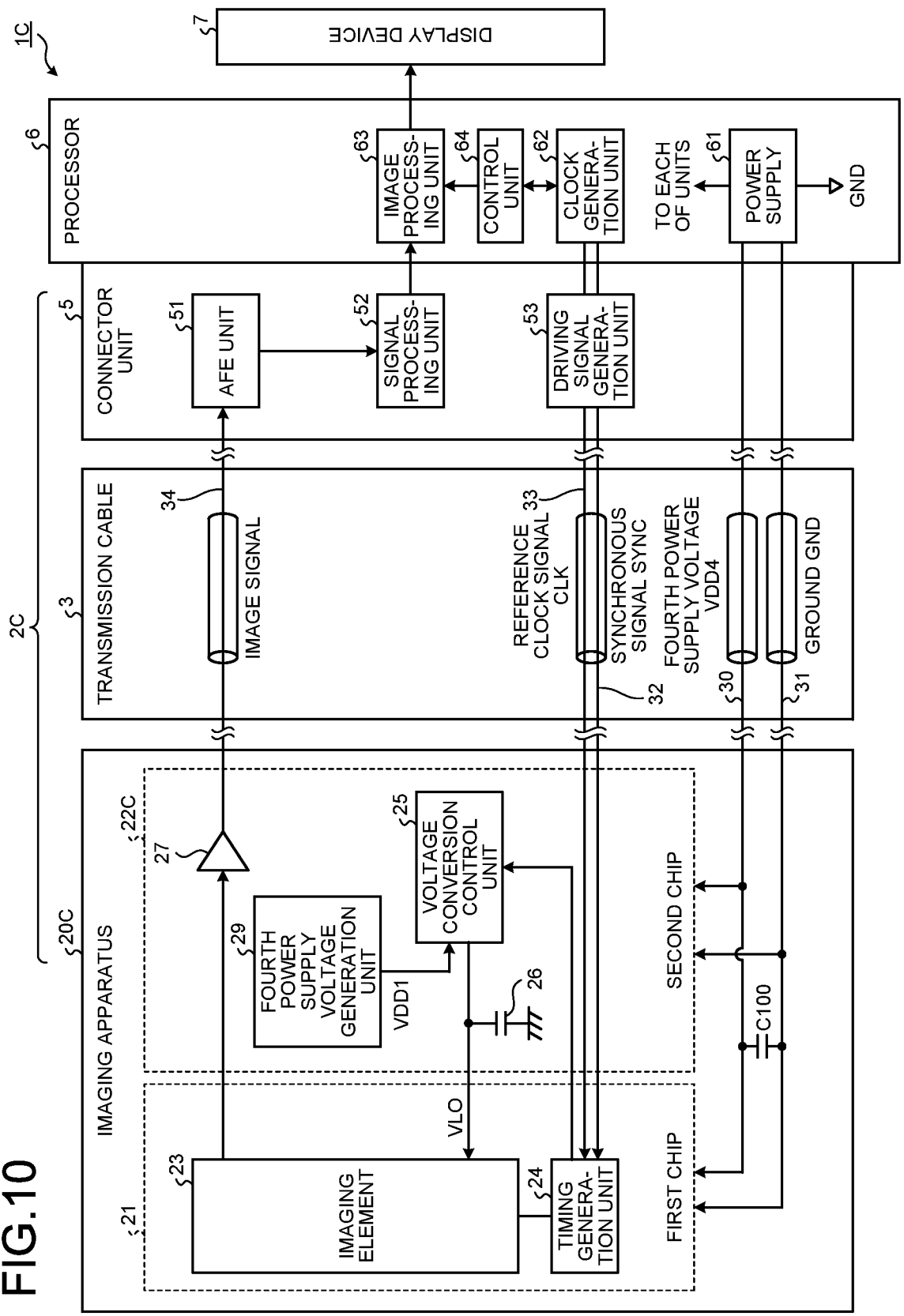
FIG. 10 is a block diagram illustrating a functional configuration of an endoscope system according to a fourth embodiment.

FIG. 10 is a block diagram illustrating a functional configuration of the endoscope system according to the fourth embodiment. An endoscope system 10 illustrated in FIG. 10 includes an endoscope 2C instead of the endoscope 2B according to the third embodiment as described above. Further, the endoscope 2C includes an imaging apparatus 20C instead of the imaging apparatus 20B according to the third embodiment as described above. Furthermore, the imaging apparatus 20C includes a second chip 22C instead of the second chip 22B according to the third embodiment as described above.

The second chip 22C further includes a fourth power supply voltage generation unit 29 in addition to the components of the second chip 22 according to the first embodiment as described above.

The fourth power supply voltage generation unit 29 generates the first power supply voltage VDD1 (VDD4>VDD1) that is lower by predetermined voltage than the power supply voltage VDD (fourth power supply voltage VDD4 in the fourth embodiment) that is input from the processor 6 via the transmission cable 3, and outputs the first power supply voltage VDD1 to the voltage conversion control circuit 25.

Figure 11:
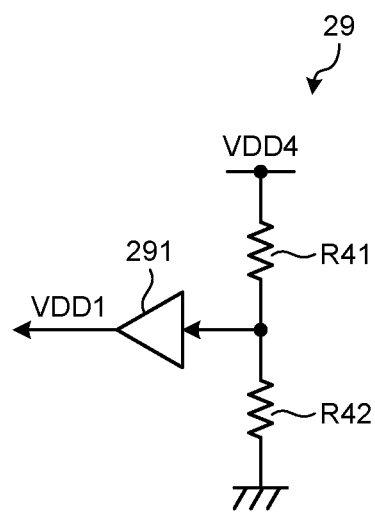
FIG. 11 is a diagram illustrating a circuit configuration of a fourth power supply voltage generation unit according to the fourth embodiment.

FIG. 11 is a diagram illustrating a circuit configuration of the fourth power supply voltage generation unit 29. As illustrated in FIG. 11, the fourth power supply voltage generation unit 29 includes a resistance R41 and a resistance R42 between the first terminal of the fourth power supply voltage VDD4 and the ground terminal of the ground voltage GND. Further, the fourth power supply voltage generation unit 29 includes a buffer 291. The fourth power supply voltage generation unit 29 performs resistance voltage dividing on a voltage difference between the fourth power supply voltage VDD4 and the ground voltage GND by using the resistance R41 and the resistance R42, and amplifies the voltage subjected to the resistance voltage dividing by using the buffer 291, to thereby generate the first power supply voltage VDD1.

According to the fourth embodiment as described above, in a case in which the first chip 21 is manufactured by using a relatively high withstand voltage semiconductor process for arranging a transistor capable of operating at any of a voltage difference among the power supply voltage VDD (the fourth power supply voltage VDD4), the ground voltage GND, and the second power supply voltage VLO, even if only a transistor and a resistance element (capacitance element) with withstand voltage equal to about a voltage difference between the fourth power supply voltage VDD4 and the ground voltage GND can be arranged through the semiconductor process used to manufacture the second chip 22C, because the fourth power supply voltage generation unit 29 generates the first power supply voltage VDD1 that is lower by predetermined voltage than the fourth power supply voltage VDD4, it is possible to arrange the voltage conversion control circuit 25 on the second chip 22C without using the high withstand voltage semiconductor process.

OTHER EMBODIMENTS

Various embodiments may be made by appropriately combining a plurality of constituent elements disclosed in the first to the fourth embodiments of the present disclosure as described above. For example, some constituent elements may be deleted from all of the constituent elements described in the first to the fourth embodiments of the present disclosure as described above. Furthermore, the constituent elements described in the first to the fourth embodiments of the present disclosure as described above may be appropriately combined.

Moreover, the control device and the light source device are separated from each other in the first to the fourth embodiments of the present disclosure, but they may be integrated with each other.

Furthermore, the endoscope system is adopted in the first to the fourth embodiments of the present disclosure, but, for example, a video microscope that captures an image of a subject, a mobile phone having an imaging function, and a tablet terminal having an imaging function may be adopted.

Moreover, the endoscope system including a flexible endoscope is adopted in the first to the fourth embodiments of the present disclosure, but an endoscope system including a rigid endoscope or an endoscope system including an industrial endoscope may be adopted.

Furthermore, the endoscope system including the endoscope that is inserted into a subject is adopted in the first to the fourth embodiments of the present disclosure, but, for example, an endoscope system including a rigid endoscope, a sinus endoscope, and an endoscope for an electric scalpel, an inspection probe, or the like may be adopted.

Moreover, in the first to the fourth embodiments of the present disclosure, the "unit" described above may be replaced with a "means", a "circuit", or the like. For example, the control unit may be replaced with a control means or a control circuit.

According to the present disclosure, it is possible to reduce the size of the apparatus.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A booster apparatus comprising
   a voltage conversion control circuit configured to generate second power supply voltage having lower negative voltage than ground voltage, based on the ground voltage, first power supply voltage having higher voltage than the ground voltage, and a driving clock signal supplied from outside, the voltage conversion control circuit including:
      a booster circuit configured to generate the second power supply voltage by boosting a predetermined level of voltage that is input from outside, at an absolute value level based on an input booster clock signal;
      a clock buffer configured to maintain the second power supply voltage at a predetermined level, generate the booster clock signal based on the driving clock signal, and output the generated booster clock signal to the booster circuit; and
   a voltage comparator that includes:
      a first voltage generation circuit configured to generate a first signal with a first voltage level based on the first power supply voltage and the second power supply voltage;
      a second voltage generation circuit configured to generate a second signal with a second voltage level based on the first power supply voltage and the ground voltage; and
      a comparison circuit configured to compare the first voltage level and the second voltage level and control input of the driving clock signal to be supplied to the clock buffer based on a comparison result.

2. The booster apparatus according to claim 1, wherein the first voltage generation circuit includes:
   a plurality of first resistance elements that are arranged between a first terminal of the first power supply voltage and a second terminal of the second power supply voltage, the plurality of first resistance elements being configured to electrically connect the first terminal and the second terminal and output the first signal by performing resistance voltage dividing on a voltage difference between the first power supply voltage and the second power supply voltage; and a switch that is arranged on a transmission path through which the plurality of first resistance elements electrically connect the first terminal and the second terminal, the switch being configured to energize the plurality of first resistance elements by entering an ON state during a blanking period of an image signal output by the booster apparatus, and the second voltage generation circuit includes
a plurality of second resistance elements that are arranged between the first terminal of the first power supply voltage and a ground terminal of the ground voltage, the plurality of second resistance elements being configured to electrically connect the first terminal and the ground terminal and output the second signal by performing resistance voltage dividing on a voltage difference between the first power supply voltage and the ground voltage.

3. The booster apparatus according to claim 2, wherein the plurality of first resistance elements and the plurality of second resistance elements are configured with a same kind of resistance element, and
a combined resistance value of the plurality of second resistance elements is equal to or larger than a predetermined multiple of a combined resistance value of the plurality of first resistance elements.

4. The booster apparatus according to claim 1, further comprising:
a first chip including an image sensor configured to generate an image signal by receiving light and performing photoelectric conversion; and
a second chip that includes
a third power supply voltage generation circuit configured to generate third power supply voltage that is lower by predetermined voltage than the first power supply voltage based on the first power supply voltage and the ground voltage; and
the voltage conversion control circuit,
wherein the voltage conversion control circuit further includes a transistor configured to operate at a voltage between the first power supply voltage and the ground voltage and operate at the third power supply voltage.

5. The booster apparatus according to claim 4, wherein the predetermined voltage is equal to or larger than a voltage difference between the ground voltage and the second power supply voltage.

6. The booster apparatus according to claim 1, further comprising:
a first chip including an image sensor configured to generate an image signal by receiving light and performing photoelectric conversion; and
a second chip including
a fourth power supply voltage generation circuit configured to generate the first power supply voltage that is lower by predetermined voltage than fourth power supply voltage based on the fourth power supply voltage and the ground voltage; and
the voltage conversion control circuit,
wherein the voltage conversion control circuit further includes a transistor and a resistance element configured to operate at a voltage between the fourth power supply voltage and the ground voltage and operate at the first power supply voltage.

7. The booster apparatus according to claim 6, wherein the predetermined voltage is equal to or larger than a voltage difference between the ground voltage and the second power supply voltage.

8. An imaging apparatus comprising:
the booster apparatus according to claim 1; and
an image sensor configured to be driven based on a second power supply voltage generated by the booster circuit.

9. An endoscope comprising:
an insertion portion to be inserted into a subject;
a booster apparatus that is arranged on a distal end portion of the insertion portion, the booster apparatus being configured to generate an image signal by capturing an image of the subject; and
a connector unit that is arranged on a proximal end side of the insertion portion and that is removably connected to a processor configured to supply ground voltage, first power supply voltage having higher voltage than the ground voltage, and a driving clock signal,
wherein the booster apparatus includes a voltage conversion control circuit configured to generate second power supply voltage having lower negative voltage than the ground voltage based on the first power supply voltage and the driving clock signal, and
the voltage conversion control circuit includes
a booster circuit configured to generate the second power supply voltage by boosting a predetermined level of voltage that is input from outside, at an absolute value level based on an input booster clock signal;
a clock buffer configured to maintain the second power supply voltage at a predetermined level, generate the booster clock signal based on the driving clock signal, and output the generated booster clock signal to the booster circuit; and
a voltage comparator that includes
a first voltage generation circuit configured to generate a first signal with a first voltage level based on the first power supply voltage and the second power supply voltage;
a second voltage generation circuit configured to generate a second signal with a second voltage level based on the first power supply voltage and the ground voltage; and
a comparison circuit configured to compare the first voltage level and the second voltage level and control input of the driving clock signal to be supplied to the clock buffer based on a comparison result.

10. A voltage conversion control method comprising:
generating second power supply voltage having lower negative voltage than ground voltage, based on ground voltage, first power supply voltage having higher voltage than the ground voltage, and a driving clock signal supplied from outside;
generating the second power supply voltage by boosting a predetermined level of voltage that is input from outside, at an absolute value level based on an input booster clock signal;
maintaining the second power supply voltage at a predetermined level;
generating the booster clock signal based on the driving clock signal;

generating a fist signal with a first voltage level based on the first power supply voltage and the second power supply voltage;
generating a second signal with a second voltage level based on the first power supply voltage and the ground voltage;
comparing the first voltage level and the second voltage level; and
controlling input of the driving clock signal to be supplied to a clock buffer based on a comparison result.

* * * * *